United States Patent [19]

Hughes et al.

[11] Patent Number: 5,322,689

[45] Date of Patent: Jun. 21, 1994

[54] TOPICAL AROMATIC RELEASING COMPOSITIONS

[75] Inventors: Timothy J. Hughes, Southbury; George E. Deckner, Trumbull, both of Conn.

[73] Assignee: The Procter & Gamble Company, Cincinnati, Ohio

[21] Appl. No.: 850,328

[22] Filed: Mar. 10, 1992

[51] Int. Cl.$^5$ .................. A61K 9/107; A61K 31/045; A61K 31/125; A61K 47/12
[52] U.S. Cl. ................................ 424/401; 514/692; 514/724; 514/728; 514/772.6; 514/853; 514/938; 514/931
[58] Field of Search ................ 424/401; 514/692, 724, 514/728, 772.6, 853, 931, 938

[56] References Cited

U.S. PATENT DOCUMENTS

| | | | |
|---|---|---|---|
| 2,798,053 | 7/1957 | Brown et al. | 260/2.2 |
| 4,509,949 | 4/1985 | Huang et al. | 586/558 |
| 4,534,960 | 8/1985 | Chavkin | 424/49 |
| 4,883,660 | 11/1989 | Blackman et al. | 424/78 |
| 4,927,631 | 5/1990 | Bates | 424/195.1 |
| 4,971,798 | 11/1990 | Coia et al. | 424/440 |
| 4,980,169 | 12/1990 | Oppenheimer et al. | 424/439 |
| 5,073,366 | 12/1991 | Beck | 514/772 |
| 5,073,371 | 12/1991 | Turner et al. | 424/59 |
| 5,087,445 | 2/1992 | Haffey et al. | 424/59 |

OTHER PUBLICATIONS

B.F. Goodrich Technical Data Sheet No. 73, Carbopol® 1342 (1984).
B.F. Goodrich Technical Bulletin SP-1, Product Data Specialty Polymers and Chemicals Division (Jul. 1982).
Clinical Otolaryngol, 1988 13, pp. 25-29; The effects of menthol isomers on nasal sensation of airflow R. Eccles, D. H. Griffiths, C. G. Newton & N. S. Tolley.
J. Pharm. Pharmacol, 1990, 42 pp. 652-654 "The effects of oral administration of (−)methol on nasal resistance to airflow and nasal sensation of airflow in subjects suffering from nasal congestion associated with the common cold" Ronald Eccles, Moltaz S. Jawad, Sara Morris.

*Primary Examiner*—Thurman K. Page
*Assistant Examiner*—James M. Spear
*Attorney, Agent, or Firm*—D. K. Dabbiere; D. C. Mohl; J. C. Rasser

[57] ABSTRACT

The present invention relates to topical aromatic releasing compositions substantially free from petrolatum and containing one or more volatile aromatic compounds selected from the group consisting of menthol, camphor and eucalyptus oil and mixtures thereof. In further embodiments, these compositions contain one or more topical actives, and are also useful for providing relief from symptoms associated with respiratory disorders.

17 Claims, No Drawings

TOPICAL AROMATIC RELEASING COMPOSITIONS

TECHNICAL FIELD

The present invention relates to improved topical oil-in-water emulsion pharmaceutical compositions having improved aesthetics which are useful for imparting aromatic actives. In particular, it relates to topical aromatic releasing compositions substantially free from petrolatum and containing one or more volatile aromatic compounds selected from the group consisting of menthol, camphor and eucalyptus oil and mixtures thereof. In further embodiments, these compositions contain one or more topical actives, and are also useful for providing relief from symptoms associated with respiratory disorders.

BACKGROUND OF THE INVENTION

The common cold, although not usually a serious illness, is a highly prevalent, discomforting and annoying infliction. The term "common cold" is applied to minor respiratory illnesses caused by a variety of different respiratory viruses. While rhinoviruses are the major known cause of common colds, accounting for approximately 30 percent of colds in adults, viruses in several other groups are also important. While immune responses occur, and infection with some respiratory tract viruses therefore could be prevented by a vaccine, development of a polytypic vaccine to cover all possible agents is impractical. Thus, the problem of controlling acute upper respiratory disease presents complex challenges, and the long-desired discovery of a single cure for the common cold is an unrealistic expectation.

Early symptoms may be minimal with only mild malaise, sore throat and nasal complaints. With rhinovirus infection, symptoms of nasal discharge, nasal congestion, and sneezing usually commence on the first day of illness and progress to maximum severity by the second or third day. Along with nasal symptoms may come sore, dry or scratchy throat and hoarseness and cough. Other symptoms may include mild burning of the eyes, loss of smell and taste, a feeling of pressure or fullness in the sinuses or ears, headache, and vocal impairment. Fever can occur, but is uncommon. Influenza infection generally includes fever, often of sudden onset and persisting for several days, and with great severity; generalized aches and pains; fatigue and weakness; and chest discomfort.

The costs of treating colds with over-the-counter medications in the United States is estimated at an annual cost of over 1.5 billion dollars. The direct costs of treatment in outpatient clinics is estimated at almost four billion dollars. Indirect costs, based on the amount of loss in wages because of restricted activity are substantially higher.

At present, only symptomatic treatment is available for the common cold; the majority of these drugs are taken orally. Exemplary prior art oral compositions for treatment of cough, cold, cold-like and/or flu symptoms and the discomfort, pain, fever and general malaise associated therewith generally contain an analgesic (aspirin or acetaminophen) and one or more antihistamines, decongestants, cough suppressants, antitussives and expectorants. For individuals with certain medical conditions such as heart disease, hypertension, diabetes or thyroid disorders, oral drugs such decongestants could pose a risk of unfavorable drug interactions and may cause an adverse reaction. It would, therefore, be highly desirable to deliver relief from these symptoms via topical compositions and thus without the need to orally ingest drugs. In addition, topical colds medications will not cause drowsiness or other side effects attendant with oral decongestants.

Prior art topical compositions containing aromatic actives effective at treating many of these symptoms such as nasal congestion and cough; however these ointment-based compositions, which generally contain high levels of petrolatum, have an undesirable greasy and tacky feel.

It is therefore an object of the present invention to provide topical aromatic releasing compositions which provide treatment for cough, cold, cold-like and/or flu symptoms. It is a further object of the present invention to provide topical aromatic releasing compositions with improved cosmetics which do not substantially affect the release of aromatic vapors. It is still a further object of the present invention to provide compositions which minimize the likelihood of adverse drug interactions and further which provide for proper medication management.

SUMMARY OF THE INVENTION

The present invention relates to a topical oil-in-water emulsion composition useful for releasing an aromatic decongestant composition substantially free from petrolatum comprising:

(a) from about 0.025% to about 3% of a carboxylic copolymer comprising polymers of a monomeric mixture selected from the group consisting of acrylic, methacrylic and ethacrylic acids, about 1 to about 3.5 weight percent of an acrylate ester of the formula:

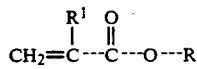

wherein R is hydrogen or an alkyl radical containing 10 to 30 carbon atoms and $R^1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups;

(b) from about 0.1% to about 30% of one or more volatile aromatic compounds selected from the group consisting of menthol, camphor and eucalyptus oil and mixtures thereof.

The present invention also relates to a method for treatment of cough, cold, cold-like and/or flu symptoms comprising administering a safe and effective amount of these topical aromatic releasing decongestant compositions.

All levels and ratios are by weight of the total composition, unless otherwise indicated.

DETAILED DESCRIPTION OF THE INVENTION

The compositions of the present invention contain the essential: components as well as various optional components as indicated below.

Aromatic Actives

The first essential component of the present invention is an aromatic active component. This aromatic active component comprises from about 0.1% to about 30%, preferably from about 1% to about 20% and most preferably from about 5% to about 15% of one or more volatile aromatic compounds selected from the group consisting of menthol, camphor and eucalyptus oil and mixtures thereof. These aromatic active components are more fully described in 53 Federal Register 30561, Aug. 12, 1988, incorporated by reference herein.

Carboxylic Acid Copolymer

Another essential component of the compositions of the present invention is a carboxylic acid copolymer (i.e. an acrylic acid copolymer). Without being limited by theory, it is believed that the compositions of the present invention emulsified with these copolymers rapidly de-emulsify on the skin thereby providing continuous oil film on the skin and good release of the aromatic actives contained herein. These copolymers consist essentially of a colloidally water-soluble polymer of acrylic acid crosslinked with polyalkenyl polyether of a polyhydric alcohol, and optionally acrylate ester or a polyfunctional vinylidene monomer.

Preferred copolymers useful in the present invention are polymers of a monomeric mixture containing 95.9 to 98.8 weight percent of an olefinically unsaturated carboxylic monomer selected from the group consisting of acrylic, methacrylic and ethacrylic acids; about 1 to about 3.5 weight percent of an acrylate ester of the formula:

wherein R is an alkyl radical containing 10 to 30 carbon atoms and $R^1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R^1$ is methyl, most preferably the acrylate ester is stearyl methacrylate. Preferably, the amount of cross-linking polyalkenyl polyether monomer is from about 0.2 to 0.4 weight percent. The preferred crosslinking polyalkenyl polyether monomers are alkyl pentaerythritol, trimethylolpropane diallylether or alkyl sucrose. These polymers are fully described in U.S. Pat. No. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials can be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

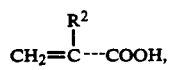

wherein $R^2$ is a substituent selected from the class consisting of hydrogen, halogen, and the cyanogen ($-C\equiv N$) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The second monomeric ingredient useful in the production of these carboxylic polymers are the polyalkenyl polyethers having more than one alkenyl ether grouping per molecule. The most useful possess alkenyl groups in which an olefinic double bond is present attached to a terminal methylene grouping, $CH_2=C<$.

The additional monomeric materials which can be present in the polymers include polyfunctional vinylidene monomeric containing at least two terminal $CH_2<$ groups, including for example, butadiene, isoprene, divinyl benzene, divinyl naphthalene, alkyl acrylates, and the like. These polymers are fully described in U.S. Pat. No. 2,798,053, to Brown, H.P., issued Jul. 2, 1957, this patent being incorporated herein by reference.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, and Acrylates/$C_{10-30}$ Alkyl Acrylate Cross Polymers (available as Carbopol® 934, Carbopol® 941, Carbopol® 950, Carbopol® 951, Carbopol® 954, Carbopol® 980, Carbopol® 981, Carbopol® 1342, the Pemulen Series, respectively, from B. F. Goodrich), and the Aculyn Series from Rohm & Haas (e.g., Aculyn 22 which is an acrylate/steareth-20, methacrylate copolymer).

Other carboxylic acid copolymers useful in the present invention include sodium salts of acrylic acid/acrylamide copolymers sold by the Hoechst Celanese Corporation under the trademark Hostaceren PN73. Also included are the hydrogel polymers sold by Lipo Chemicals Inc. under the trademark of HYPAN hydrogels. These hydrogels consist of crystalline plicks of nitrites on a C-C backbone with various other pendant groups such as carboxyls, amides, and amidines. An example would include HYPAN SA100 H, a polymer powder available from Lipo Chemical.

The carboxylic acid copolymers can be used individually or as a mixture of two or more polymers and comprise from about 0.025% to about 3%, preferably from about 0.1% to about 1.50% and most preferably from about 0.2% to about 1.25% of the compositions of the present invention.

Pharmaceutical Carrier

The pharmaceutical compositions of the present invention may be made into a wide variety of product types having a pharmaceutically-acceptable emulsion base.

The pharmaceutical compositions of the present invention formulated as creams typically include a pharmaceutically or cosmetically-acceptable organic solvent. The terms "pharmaceutically-acceptable organic solvent" and "cosmetically-acceptable organic solvent" refer to an organic solvent which also possesses acceptable safety (e.g. irritation and sensitization characteristics), as well as good aesthetic properties (e.g., does not feel greasy or tacky). The most typical example of such a solvent is water. Examples of other suitable organic solvents include: propylene glycol, polyethylene glycol (200-600) polypropylene glycol (425-2025), glycerol, 1,2,4-butanetriol, sorbitol esters, 1,2,6-hexanetriol, ethanol, isopropanol, butanediol, and mixtures thereof.

The composition may also comprise from about 2% to about 10% of an emollient plus from about 0.1% to about 2% of a thickening agent. Examples of suitable thickening agents include: cellulose derivatives (e.g., methyl cellulose and hydroxy propylmethyl cellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers are described in detail in U.S. Patent 2,798,053, Brown, issued Jul. 2, 1975, incorporated herein by reference). A more complete disclosure of thickening agent useful herein can be found in Segatin, *Cosmetics, Science and Technoloqy*, 2nd Edition, Vol. 1, pp. 72-73 (1972), incorporated herein by reference.

The composition may optionally comprise from about 1% to about 10%, preferably from about 2% to about 5%, of an additional emulsifier. These emulsifiers may be nonionic, anionic or cationic. Suitable emulsifiers are disclosed in, for example, U.S. Pat. No. 3,755,560, issued Aug. 28, 1973, Dicert et al.; U.S. Pat. No. 4,421,769, issued Dec. 20, 1983, Dixon et al.; and McCutcheon's *Detergents and Emulsifiers*, North American Edition, pages 317-324 (1986); the disclosures of which are incorporated herein by reference. Preferred emulsifiers are anionic or nonionic, although the other types may also be used.

Single emulsion skin care preparations, such as lotions and creams, of the oil-in-water type and water-in-oil type are well-known in the cosmetic art and are useful in the present invention. Multiphase emulsion compositions, such as the water-in-oil-water type, as disclosed in U.S. Pat. No. 4,254,105, Fakuda et al., issued March 3, 1981, herein incorporated by reference, are also useful in there present invention. In general, such single or multiphase emulsions contain water, emollients and emulsifiers an essential ingredients.

Triple emulsion carrier systems comprising an oil-in-water-in-silicone fluid emulsion composition as disclosed in U.S. patent application Ser. No. 022,876, Figueroa, et al., filed Mar. 6, 1987, herein incorporated by reference, are al so useful in the present invention. This triple emulsion carrier system can be combined with from about 1% to about 20%, preferably from about 2% to about 10%, of the chelating agent to yield the pharmaceutical composition of the present invention.

Another emulsion carrier system useful in the pharmaceutical compositions of the present invention is a microemulsion carrier system. Such a system comprises from about 9% to about 15% squalene; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with from about 2% to about 10% of the chelating agent.

Optional Components

Emollients

The compositions of the present invention preferably comprise at least one emollient. Useful emollients have a required HLB below about 10. Preferred emollients are volatile silicone oils, non-volatile emollients, and the highly branched hydrocarbons known as the Permethyl 99 through 108A series (available from Permethyl Corporation) and mixtures thereof. The compositions of the present invention more preferably comprise at least one volatile silicone oil which functions as a liquid emollient, or especially in a mixture of volatile silicone oils and non-volatile emollients. The term "volatile", as used herein, refers to those materials which have a measurable vapor pressure at ambient temperature.

Volatile silicone oils useful in the compositions of the present invention are preferably cyclic. The following formula illustrates cyclic volatile polydimethylsiloxanes useful in the compositions disclosed herein:

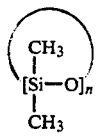

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries*, 91, pages 27-32 (1976), the disclosures of which are incorporated by reference herein in their entirety.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The present compositions also preferably contain one or more non-volatile emollients. Such materials include fatty acid and fatty alcohol esters, hydrocarbons, non-volatile silicone oils, and mixtures thereof. Emollients among those useful herein are described in 1 *Cosmetics,*

Science and Technology 27–104 (M. Balsam and E. Sagatin, Ed.; 1972), and U.S. Pat. No. 4,202,879, to Shelton issued May 13, 1980 (both incorporated by reference herein).

Non-volatile silicone oils useful as an emollient material include polyalkylsiloxanes and polyalklyarylsiloxanes. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include polymethylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation).

Non-polar fatty acid and fatty alcohol esters useful herein as an emollient material include, for example, ethyl hexyl palmitate, isodecyl neopentanoate, octadodecyl benzoate, diethyl hexyl maleate and PPG-2 myristyl ether propionate. Hydrocarbons such as isohexadecane (e.g., Permethyl 101A supplied by Presperse), petrolatum and USP light (e.g. Klearol®) or heavy (e.g. Kaydol®) mineral oils are also useful as emollients. Emollients useful in the instant invention are further described in U.S. Pat. No. 4,919,934, to Decknet et al., issued Apr. 24 1990, which is incorporated herein by reference in its entirety.

The emollients typically comprise in total from about 1% to about 50%, preferably from about 1% to about 25%, and more preferably from about 1% to about 10% by weight of the compositions of the present invention.

Humectants/Moisturizers

The compositions of the instant invention can also contain one or more humectants/moisturizers. A variety of humectants/moisturizers can be employed and can be present at a level of from about 1% to about 10%, more preferably from about 2% to about 8% and most preferably from about 3% to about 5%. These materials include urea; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerin, hexanetriol, propylene glycol, hexylene glycol and the like; polyethylene glycol; sugars and starches; sugar and starch derivatives (e.g. alkoxylated glucose); D-panthenol; hyaluronic acid; lactamide monoethanolamine; acetamide monoethanolamine; and mixtures thereof.

Preferred humectants/moisturizers for use in the compositions of the present invention are the $C_3$–$C_6$ diols and triols. Especially preferred is the triol, glycerin.

Pharmaceutical Actives

Pharmaceutical actives useful in the present invention include any chemical material or compound suitable for topical administration; however, such drugs should be included so as not to interfere with the stability of the composition. These actives are present at a level from about 0.1% to about 20%. Such substances include, but are not limited to antibiotics, wound healing agents, vitamins, antiviral agents, analgesics, anti-inflammatory agents, antipuritics, antipyretics, anesthetic agents, antifungals, antimicrobials, and mixtures thereof.

A safe and effective amount of an anti-inflammatory agent may be added to the compositions of the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednyl idene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chloroprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the present invention is hydrocortisone.

A second class of anti-inflammatory agents which is useful the compositions of the present invention includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts including *Anti-inflammatory and Anti-Rheumatic Drugs*, K. D. Rainsford, Vol. I-III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in composition of the present invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazone, and trimethazone Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamlc acid, meclofenamic acid, piroxicam and felbinac are preferred; ibuprofen, naproxen, and flufenamic acid are most preferred.

Another class of anti-inflammatory agents which are useful in the present invention are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compound s selected from 4-(4'-pentyn-3'-one)-2,6-di-t-butylphenol; 4-(5'-hexynoyl)-2,6-di-t-butyl phenol; 4-((S)-(-)-3'-methyl-5'-hexynoyl)-2,6-di-t-butyl phenol; 4-((R)-(+)-3'-methyl-5'-hexynoyl)-2,6-di-t-butylphenol; and 4-(3',3'-dimethoxypropionyl)-2,6-di-t-butylphenol are useful in the present invention.

Yet another class of anti-inflammatory agents which are useful in the present invention are those disclosed in U.S. Pat. No. 4,912,248, Mueller, issued Mar. 27, 1990. This patent discloses compounds and diastereomeric mixtures of specific 2-naphthyl-containing ester compounds, especially naproxen ester and naproxol ester compounds, having two or more chiral centers.

Finally, so-called "natural" anti-inflammatory agents are useful in the present invention. For example, candelilla wax, alpha bisabolol, aloe vera, Manjistha (extracted from plants in the genus Rubia, particularly Rubia Cordifolia), and Guggal (extracted from plants in the genus Commiphora, particularly Commiphora Mukul), may be used.

Useful anesthetic or antipruritic drugs are selected from the group consisting of lidocaine, lidocaine hydrochloride, bupivacaine hydrochloride, chlorprocaine hydrochloride, dibucaine hydrochloride, etidocaine hydrochloride, mepivacaine hydrochloride, tetracaine, tetracaine hydrochloride, dyclonine hydrochloride and hexylcaine hydrochloride, benzocaine, benzyl alcohol, butamben picrate, camphor, camphorated metacresol, dibucaine, dibucaine hydrochloride, dimethisoquin hydrochloride, diphenhydramine hydrochloride, juniper tar, menthol, phenol, phenolate sodium, pramoxine hydrochloride, resorcinol and mixtures thereof.

Vitamins

Various vitamins may also be included in the topical compositions the present invention. For example, Vitamin A, and derivatives thereof, ascorbic acid, Vitamin B, biotin, panthothenic acid, Vitamin D, and mixtures thereof may be used. Vitamin E, tocopherol acetate and derivatives may also be used.

Aromatics

Various other non-active aromatic components (e.g., aldehydes and esters) may also be used. These aromatics include, for example, benzaldehyde (cherry, almond); citral (lemon, lime); neral; decanal (orange, lemon); aldehyde C-8, aldehyde C-9 and aldehyde C-12 (citrus fruits); tolyl aldehyde (cherry, almond); 2,6-dimethyl-octanal (green fruit); and 2-dodecenal (citrus, mandarin). Mixtures of these aromatics can also be used.

Other Optional Components

A variety of additional ingredients may be added to the emulsion compositions of the present invention. These additional ingredients include various polymers for aiding the film-forming properties and substantivity of the formulation, preservatives for maintaining the antimicrobial integrity of the compositions, antioxidants, and agents suitable for aesthetic purposes such as fragrances, pigments, and colorings.

The compositions can also contain low levels of insoluble ingredients added, for example for visual effect purposes, e.g. thermochromic liquid crystalline materials such as the microencapsulated cholesteryl esters and chiral nematic (nonsterol) based chemicals such as the (2-methylbutyl) phenyl 4-alkyl(oxy)benzoates available from Hallcrest, Glenview, Ill. 60025, U.S.A.

The pH of the compositions is preferably from about 5 to about 9, more preferably from about 6.5 to about 8.

The amount of active components and frequency of treatment will vary widely depending upon the individual.

Preferably the composition is applied to the skin via topical application of a safe and effective amount of the composition to treat cough, cold, cold-like and/or flu symptoms. The amount of actives and frequency of topical application to the skin can vary widely, depending upon personal needs, but it is suggested as an example that topical application range from about once per day to about four times daily, preferably from about twice per day to about three times daily with use of from about 0.2 grams to about 17.4 grams, preferable from about 2.5 grams to about 7.5 grams of the composition per dose. The amount of aromatic agents applied is generally from about 1.0 mg to about 10.0 mg per $cm^2$ skin.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

| Ingredients | W/W % |
|---|---|
| 1-Menthol | 2.81 |
| Camphor | 5.23 |
| Eucalyptus Oil | 1.34 |
| Cedarleaf Oil | 0.44 |
| Myristica Oil | 0.69 |
| Thymol | 0.09 |
| Turpentine | 2.00 |
| PEG-100 Stearate | 0.31 |
| Cetyl Palmitate | 3.00 |
| Stearyl Alcohol | 1.50 |
| Dimethicone | 0.63 |
| Cetyl Alcohol | 2.25 |
| Stearic Acid | 0.31 |
| Isopropyl Palmitate | 1.25 |
| Carbomer 954[1] | 0.75 |
| Glycerin | 10.00 |
| Titanium Dioxide | 0.15 |
| Cyclomethicone and Dimethicone Copolyol | 1.88 |

-continued

| Ingredients | W/W % |
| --- | --- |
| Sodium Hydroxide | 0.42 |
| Disodium EDTA | 0.10 |
| Propylparaben | 0.10 |
| Methylparaben | 0.25 |
| Water, Purified | 64.50 |

[1] Available as Carbopol 954 from B. F. Goodrich

In a suitable size vessel, add the PEG-100 stearate, cetyl palmitate, stearyl alcohol, dimethicone, cetyl alcohol, stearic acid, isopropyl palmitate and propylparaben. While mixing, heat to about 75° C., continue mixing until clear. In a suitable size vessel, add a portion of the water, carbomer, titanium dioxide and some of the glycerin, while mixing heat to about 70° C. While mixing, add the oil phase to the water phase, then add the cyclomethicone/dimethicone copolyol and the disodium EDTA. In a suitable size container mix the methylparaben, the remainder of the glycerin and some water and add to batch. In a suitable size container, add the methanol, camphor, eucalyptus oil, cedarleaf oil, myristica oil, thymol and turpentine with gentle mixing. Add the aromatic mixture to the batch. Cool batch to 40° C. and add sodium hydroxide solution. Pass resulting mixture through a mill (such as, for example, a Tek Mar mill).

Use of approximately five grams of the composition is useful for topical application to provide relief from cough, cold, cold-like and/or flu symptoms.

| Ingredients | W/W % |
| --- | --- |
| Water, purified | 73.50 |
| Hydroxypropyl Methylcellulose | 0.10 |
| Glycerin | 4.00 |
| Polysorbate 80 | 0.40 |
| Disodium EDTA | 0.10 |
| Imidazolidinyl Urea | 0.20 |
| Methylparaben | 0.25 |
| Propylparaben | 0.15 |
| Polyglyceryl-10 Decaoleate | 4.00 |
| Octyl Hydroxystearate | 3.00 |
| Isostearyl Benzoate | 2.50 |
| Camphor | 5.25 |
| L-Menthol | 2.75 |
| Lavender Oil | 2.15 |
| L-Bornyl Acetate | 0.25 |
| Dimethicone | 0.50 |
| Acrylates/C$_{10}$-C$_{30}$ Alkyl Acrylate Crosspolymer[1] | 0.20 |
| Carbomer 981[2] | 0.30 |
| Triethamolamine | 0.40 |

[1] Available as Pemulen TR-1 from B. F. Goodrich
[2] Available as Carbopol 981 from B. F. Goodrich In a suitable size vessel, combine the water, hydroxypropyl methylcellulose, glycerin, polysorbatet 80, disodium EDTA, imidazolidinyl urea and methylparaben using rapid agitation and heat to about 60° C. In a separate vessel, combine the propylparaben, polyglyceryl-10 decaoleate, octyl hydroxystearate, isosteayl benzoate, camphor, menthol, lavender oil, bornyl acetate, dimethicone, Pemulen TR-1 and carbomer, mix using rapid agitation until uniform and heat to about 60° C. Slowly add the oil phase to the water phase while mixing with moderate agitation. Add the triethanolamine and mix vigorously. Cool resulting mixture to room temperature.

Use of approximately five grams of the composition is useful for topical application to provide relief from cough, cold, cold-like and/or flu symptoms.

| Ingredients | W/W % |
| --- | --- |
| Water, purified | 61.45 |
| Carbomer 1342[1] | 0.20 |
| Glycerin | 1.00 |
| L-Menthol | 10.00 |
| Methyl Salicylate | 15.00 |
| Steareth-21 | 1.00 |
| Steareth-2 | 0.75 |
| Isodecyl Neopentanoate | 8.00 |
| Imidazolidinyl Urea | 0.10 |
| Methylparaben | 0.30 |
| Propylparaben | 0.15 |
| Disodium EDTA | 0.10 |
| Cetyl Alcohol | 1.00 |
| Stearyl Alcohol | 0.75 |
| Triethanolamine | 0.20 |

[1] Available as Carbopol 1342 from B. F. Goodrich

Combine the carbomer 1342, glycerin, methylparaben and imidazolidinyl urea with water while mixing and heating to 75° C. The triethanolamine is combined to this mixture and the resulting mixture is heated to about 80° C. In a separate vessel, combine menthol, methyl salicylate, steareth-21, steareth-2, isodecyl neopentanoate, propyl paraben, cetyl alcohol and stearyl alcohol. While mixing, heat this mixture to about 80° C. to form the oil phase. Add the oil phase to the water phase while mixing (high shear, for example, a Lightnin' mixer). Add the disodium EDTA and cool the resulting mixture to room temperature.

What is claimed is:

1. A topical composition useful for releasing an aromatic decongestant composition substantially free from petrolatum comprising:
   (a) from about 0.025% to about 3% of a carboxylic copolymer comprising polymers of a monomeric mixture selected from the group consisting of acrylic, methacrylic and ethacrylic acids, about 1 to about 3.5 weight percent of an acrylate ester of the formula:

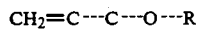

wherein R is hydrogen or an alkyl radical containing 10 to 30 carbon atoms and $R^1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups;
   (b) from about 0.1% to about 30% of one or more volatile aromatic compounds selected from the group consisting of menthol, camphor and eucalyptus oil and mixtures thereof wherein said composition is in the form of an oil-in-water emulsion.

2. A topical aromatic releasing composition according to claim 1 the polymer component contains from about 96 to about 97.9 weight percent of acrylic acid and from about 2.5 to about 3.5 weight percent of acrylic esters wherein the alkyl group contains 12 to 22 carbon atoms, and $R_1$ is methyl.

3. A topical aromatic releasing composition according to claim 2 wherein the acrylate ester of the carboxylic copolymer is stearyl methacrylate, and wherein the copolymer comprises from about 0.2 to 0.4 weight percent of the crosslinking monomer selected from the group consisting of allyl pentaerythritol, trimethylolpropane diallylether or allyl sucrose.

4. A topical aromatic releasing composition according to claim 3 which further comprises from about 0.1% to about 20% of a humectant.

5. A topical aromatic releasing composition according to claim 4 which further comprises from about 0.1% to about 20% of a pharmaceutical active.

6. The composition of claim 5 wherein said pharmaceutical active is selected from the group consisting of antimicrobials, wound healing agents, vitamins, antiviral agents, analgesics, anti-inflammatory agents, antipuritics, antipyretics, anesthetic agents, antifungals, antimicrobials and mixtures thereof.

7. The composition of claim 5 wherein said antimicrobial drug is selected from the group consisting of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine, pharmaceutically-acceptable salts thereof and mixtures thereof.

8. The composition of claim 5 wherein said anesthetic or antipruritic drug is selected from the group consisting of lidocaine, lidocaine hydrochloride, bupivacaine hydrochloride, chlorprocaine hydrochloride, dibucaine hydrochloride, etidocaine hydrochloride, mepivacaine hydrochloride, tetracaine, tetracaine hydrochloride, dyclonine hydrochloride and hexylcaine hydrochloride, benzocaine, benzyl alcohol, butamben picrate, camphor, camphorated metacresol, dibucaine, dibucaine hydrochloride, dimethisoquin hydrochloride, diphenhydramine hydrochloride, juniper tar, menthol, phenol, phenolate sodium, pramoxine hydrochloride, resorcinol and mixtures thereof.

9. The composition of claim 5 wherein said non-steroidal anti-inflammatory drug is selected from the group consisting of propionic acid derivatives, acetic acid derivatives, fenamic acid derivatives, biphenylcarboxylic acid derivatives, and oxicams and mixtures thereof 10. The composition of claim 5 wherein said non-steroidal anti-inflammatory drug is a propionic acid derivatives selected from the group consisting of aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid and mixtures thereof.

11. The composition of claim 5 wherein said vitamin is selected from the group consisting of Vitamin A, and derivatives thereof, ascorbic acid, Vitamin B, biotin, panthothenic acid, Vitamin D, Vitamin E and mixtures thereof.

12. The composition of claim 5 which further comprises an additional aromatic from the group consisting of benzaldehyde, citral, neral, decanal, aldehyde C-8, aldehyde C-9, aldehyde C-12, tolylaldehyde, 2,6-dimethyl-octanal and 2-dodecenal and mixtures thereof.

13. A method for treatment of cough, cold, cold-like and/or flu symptoms comprising administering a safe and effective amount of the topical aromatic releasing decongestant composition of claim 1.

14. A method for treatment of cough, cold, cold-like and/or flu symptoms comprising administering a safe and effective amount of the topical aromatic releasing decongestant composition of claim 2.

15. A method for treatment of cough, cold, cold-like and/or flu symptoms comprising administering a safe and effective amount of the topical aromatic releasing decongestant composition of claim 5.

16. A method for treatment of cough, cold, cold-like and/or flu symptoms comprising administering a safe and effective amount of the topical aromatic releasing decongestant composition of claim 8.

17. A method for treatment of cough, cold, cold-like and/or flu symptoms comprising administering a safe and effective amount of the topical aromatic releasing decongestant composition of claim 10.

* * * * *